US00PP10018P

United States Patent [19]

Lemon

[11] Patent Number: Plant 10,018

[45] Date of Patent: Sep. 2, 1997

[54] VARIETY OF GERANIUM PLANT NAMED 'GYPSY GIRL'

[75] Inventor: David Lemon, Lompoc, Calif.

[73] Assignee: John Bodger and Sons Company, South El Monte, Calif.

[21] Appl. No.: 571,163

[22] Filed: Dec. 12, 1995

[51] Int. Cl.[6] ..... A01H 5/00

[52] U.S. Cl. ..... Plt./87.12

[58] Field of Search ..... Plt./87.12

[56] References Cited

U.S. PATENT DOCUMENTS

P.P. 6,017 9/1987 Kirmann ..... Plt./87.12

*Primary Examiner*—Howard J. Locker

*Attorney, Agent, or Firm*—Fulwider Patton Lee & Utecht, LLP

[57] ABSTRACT

The cultivar is characterized by its very pale purple color. Its compact, controlled growth habit and prolific blooms provide for superb cuttings and performs equally well in hanging baskets or in a ground bed. The blooms are heat tolerant.

1 Drawing Sheet

BACKGROUND OF THE NEW PLANT

The present invention comprises a new and distinct cultivar of *Pelargonium×hortorium* known by the varietal name Gypsy Girl (Oglevee No. 903b, Bodger No. 9GM 58-1). The new variety was discovered in a selective breeding program by David Lemon at Bodger Seeds, Ltd., Lompoc, Calif. The new variety is a selection from the crossing of Jackpot Wild Rose (unpatented variety)×Bodger No. 7GM 331-1. Jackpot Wild Rose is distinguished from Gypsy Girl by its deep rose color. Gypsy Girl, on the other hand, has very pale purple colored flowers.

The new cultivar was first asexually reproduced by cuttings at Oglevee Ltd., Connellsville, Pa. and has been repeatedly asexually reproduced by cuttings at Oglevee Ltd. in Connellsville, Pa. It has been found to retain its distinctive characteristics through successive propagations.

The new cultivar, when grown in a glass greenhouse in Connellsville, Pa., using full light, 60° Fahrenheit night temperature, 68° Fahrenheit day temperature, 72° Fahrenheit vent temperature and grown in a soilless media of constant fertilizer 200 to 250 parts per million of nitrogen and potassium has a response time of six weeks from the rooted cutting to a flowering plant in a 10.0 cm pot.

DESCRIPTION OF THE DRAWING

The accompanying drawing illustrates the new cultivar, the color being as nearly true as possible with color illustrations of this type.

DESCRIPTION OF THE NEW PLANT

The following detailed description sets forth characteristics of the new cultivar. The data which defines each characteristic was collected from asexual reproductions carried out by Oglevee Ltd. in Connellsville, Pa. The plant histories were taken on rooted cuttings potted on Feb. 15, 1995 and flowered Apr. 1, 1995 under full light and greenhouse, and colorings were taken indoors under 200–220 foot candles of fluorescent cool white light using the R.H.S. Colour Chart of The Royal Horitcultural Society of London.

THE PLANT

Classification:

*Botanical.*—*Pelargonium×hortorum.*

Form: Semi-dwarf, uniform mound with some lateral growth.

*Height.*—15.0–17.0 cm from the media surface.

*Growth.*—Free basal branching, mound habit with some cascading growth.

*Strength.*—Free standing; free and early flowering.

Foliage: Zone present, stalked leaf attachment.

Leaves:

*Size.*—7.0–10.0 cm across.

*Shape.*—Reniform; cordate base.

*Margin.*—Crenate.

*Texture.*—Lightly pubescent, slightly reflective.

*Color.*—Top: Green Group 137C; Zone: Grayed/Purple Group 183A; Bottom: Green Group 137C.

*Ribs and veins.*—Palmate venation: Color: Green Group 139C.

Petioles:

*Length.*—5.0–7.0 cm.

*Color.*—Green group 139C.

Stem:

*Color.*—Green Group 139C.

*Internodes.*—1.0–2.0 cm in length.

THE BUD

Shape: Upright; hemispherical cluster; elliptical floret 0.9–1.0 cm in length at first tint of color.

Size: 2.6–3.5 cm across.

INFLORESCENCE

Blooming habit: Continuous, floriferous blooming.

Size: Fully open bloom 5.5–7.5 cm across.

Borne: Floret on pedicel; pedicel on peduncle; 4.5–6.6 cm above foliage.

Florets:

*Number.*—About 19 florets per head.

*Form.*—Flat to slightly cupped.

*Color.*—Top: Purple Group 75C; Bottom: Purple Group 73D.

*Petals.*—7–14 in number; separate, not united; margin entire; obovate, flat to slightly cupped.

*Size.*—1.8–2.0 cm across.

*Texture and appearance.*—Smooth and satiny. Appearance from a distance is a very delicate light purple flower above medium green foliage with a zone present.

Petaloids:

*Quantity.*—1 to 5.

*Shape.*—Narrow, elongated, some twisted.

*Color.*—Top: Purple Group 75C; Bottom: Purple Group 73C.

Pedicel:

*Length.*—2.0–2.5 cm.

*Color.*—Green Group 139C with a blush of Grayed/Red Group 181C at the flower end.

Peduncle: Arises from node opposite leaf petiole.

*Length.*—10.0–16.6 cm in length.

*Color.*—Green Group 144A.

Persistence:

*Disease resistance.*—Not known.

*Lasting quality.*—Continuous blooming habit, heat tolerant.

REPRODUCTIVE ORGANS

Stamens:

*Anthers.*—2.0–2.2 mm in length.

*Filaments.*—5.0–7.0 mm in length; flat, narrow; white.

*Pollen.*—Golden Brown.

Pistils:

*Number.*—One.

*Length.*—5.0–7.0 mm.

*Stigma.*—5–6 parted, red/purple color.

*Style.*—2.0–3.0 mm.

Ovaries: Superior, pubescent; pale green in color, 2.0 mm in length, 2.0 mm across.

Fruit: None observed.

GENERAL CHARACTERISTICS

Gypsy Girl offers a new, very pale purple color flower. Gypsy Girl produces a very large flower display above a medium green foliage. The growth habit will perform well in containers, ground beds or hanging baskets. Growing ease and abundant cutting production is similar to the current variety Elizabeth (U.S. Plant Pat. No. 8,192). Elizabeth is distinguished from Gypsy Girl by its red flowers and medium dark leaves. Gypsy Girl, on the other hand, has very pale purple flowers.

I claim:

1. A new and distinct variety of Geranium plant, substantially as shown and described.

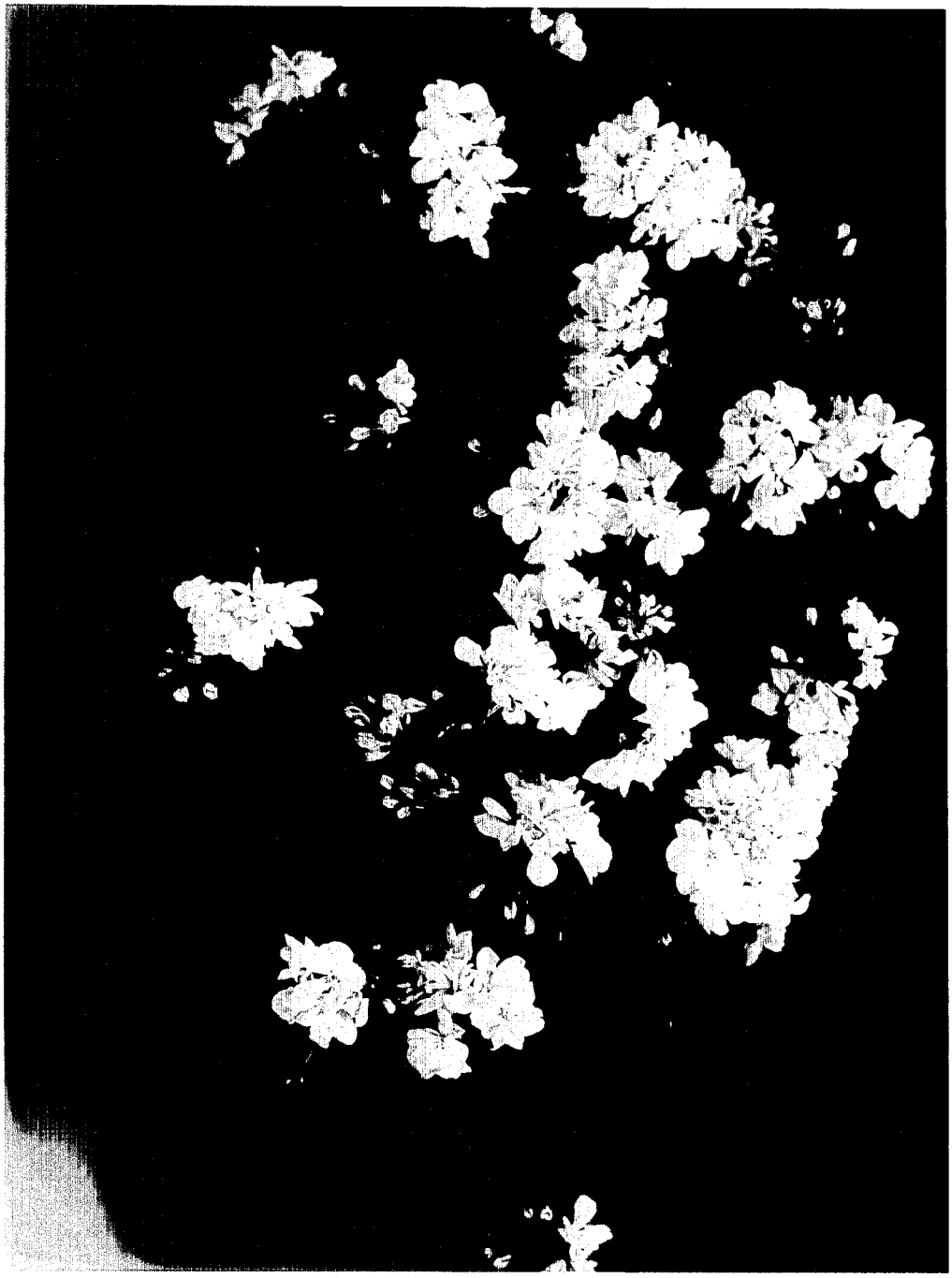

* * * * *